(12) United States Patent
Janna et al.

(10) Patent No.: US 9,855,081 B2
(45) Date of Patent: Jan. 2, 2018

(54) FIBER-REINFORCED COMPOSITE ORTHOPAEDIC DEVICE HAVING EMBEDDED ELECTRONICS

(75) Inventors: Sied W. Janna, Memphis, TN (US); James K. Rains, Cordova, TN (US); Nicholas S. Ritchey, Collierville, TN (US); Darren James Wilson, York (GB)

(73) Assignee: SMITH & NEPHEW, INC., Memphis, TN (US)

( * ) Notice: Subject to any disclaimer, the term of this patent is extended or adjusted under 35 U.S.C. 154(b) by 695 days.

(21) Appl. No.: 14/232,948

(22) PCT Filed: Jul. 13, 2012

(86) PCT No.: PCT/US2012/046659
§ 371 (c)(1),
(2), (4) Date: May 12, 2015

(87) PCT Pub. No.: WO2013/012717
PCT Pub. Date: Jan. 24, 2013

(65) Prior Publication Data
US 2015/0257799 A1    Sep. 17, 2015

Related U.S. Application Data

(60) Provisional application No. 61/508,397, filed on Jul. 15, 2011.

(51) Int. Cl.
*A61B 17/72* (2006.01)
*A61B 19/00* (2006.01)
(Continued)

(52) U.S. Cl.
CPC .............. *A61B 17/72* (2013.01); *A61B 90/06* (2016.02); *A61F 5/05* (2013.01); *A61B 17/80* (2013.01); *A61B 2017/0003* (2013.01); *A61B 2017/00022* (2013.01); *A61B 2090/064* (2016.02); *A61F 2002/4666* (2013.01)

(58) Field of Classification Search
CPC ... A61B 17/72; A61B 90/06; A61B 2090/064; A61F 5/05
See application file for complete search history.

(56) References Cited

U.S. PATENT DOCUMENTS 5,571,202 A * 11/1996 Mathys, Sr. ........ A61F 2/30767
623/23.27
5,695,496 A * 12/1997 Orsak .................... A61B 17/60
606/54

(Continued)

FOREIGN PATENT DOCUMENTS

CN    102123657A A    7/2011
WO    2010/045473 A2    4/2010

OTHER PUBLICATIONS

Chinese Patent Office, Third Office Action dated Apr. 25, 2016, with English translation, 15 pages.
Chinese Patent Office, First Office Action dated Dec. 12, 2014, with English translation, 16 pages.

(Continued)

*Primary Examiner* — Christian Sevilla

(57) ABSTRACT

In one general aspect, an orthopedic fixation device includes an inner core and shaft formed of a multi-layered, fiber-reinforced composite. A sensing element is embedded within the multi-layered, fiber-reinforced composite.

19 Claims, 11 Drawing Sheets

(51) Int. Cl.
*A61F 5/05* (2006.01)
*A61B 17/80* (2006.01)
*A61B 17/00* (2006.01)
*A61F 2/46* (2006.01)
*A61B 90/00* (2016.01)

(56) References Cited

U.S. PATENT DOCUMENTS

| | | | | |
|---|---|---|---|---|
| 8,388,553 | B2 * | 3/2013 | James | A61B 5/0031 600/587 |
| 2004/0204647 | A1 * | 10/2004 | Grupp | A61B 5/0031 600/431 |
| 2008/0077016 | A1 * | 3/2008 | Sparks | A61B 5/0031 600/459 |
| 2010/0274121 | A1 * | 10/2010 | Ritchey | A61B 5/05 600/424 |
| 2011/0152725 | A1 * | 6/2011 | Demir | A61B 5/0031 600/587 |

OTHER PUBLICATIONS

Extended European search report dated Jan. 27, 2015, 6 pages.
Chinese Patent Office, Second Office Action dated Sep. 11, 2015, with English translation, 17 pages.
Chinese Patent Office, Decision on Rejection dated Dec. 29, 2016, 18 pages including English translation.
European Patent Office, First Office Action dated Feb. 16, 2017, 4 pages.
Notification of Reexamination for Chinese Application No. 201280045142.9, dated Aug. 9, 2017, with English translation.

* cited by examiner

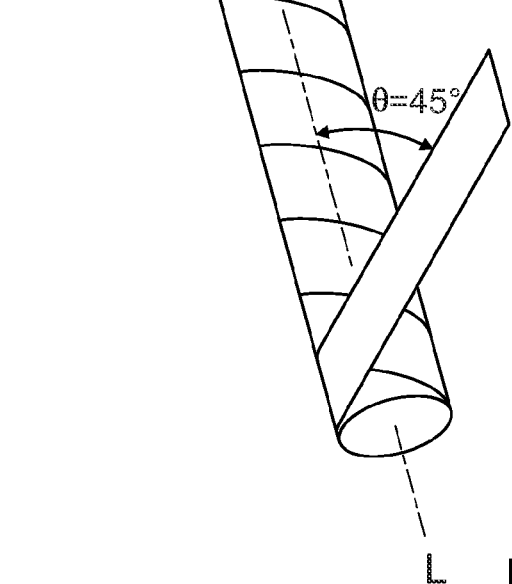
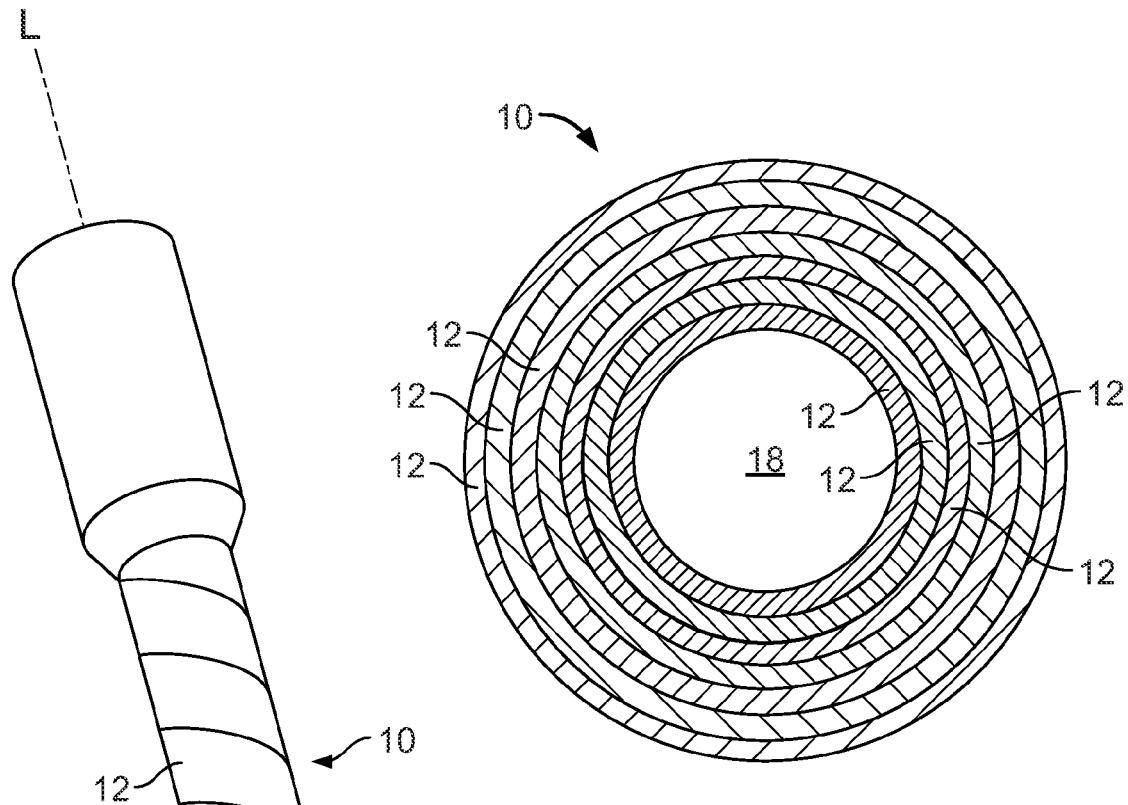
FIG. 1
FIG. 2

FIBER-REINFORCED COMPOSITE ORTHOPAEDIC DEVICE HAVING EMBEDDED ELECTRONICS

CROSS-REFERENCE TO RELATED APPLICATIONS

This application is a United States National Phase filing of International Application No. PCT/US2012/046659 filed on Jul. 13, 2012 which claims priority to and the full benefit of U.S. Provisional Application Ser. No. 61/508,397, filed Jul. 15, 2011, and titled "FIBER-REINFORCED COMPOSITE ORTHOPAEDIC DEVICE HAVING EMBEDDED ELECTROINCS," the entire contents of which are incorporated herein by reference.

TECHNICAL FIELD

This disclosure relates to orthopaedic devices.

BACKGROUND

Multi-layered composite materials have been used in orthopaedic fixation devices. Thermoplastic and thermoset fiber-reinforced composite materials have been used to reinforce, repair or even replace metallic structures. When used in orthopaedic devices, composite structures should be monitored independently from their domain of use (e.g., the surrounding bone or other tissue), especially for load-bearing structures to avoid catastrophic failures resulting from structural cracking, delamination, and de-bonding of the fibers from the matrix. High-strength composite materials are often manufactured in the form of tapes or sheets, otherwise known as pre-impregnated materials or "pre-preg," and accordingly, generally require sensors or "smart strips" that are embedded within the structure, depending upon the structural layer that has to be monitored. In the case of cannulated orthopaedic implants, these sensors are generally placed as far as possible from the neutral axis to ensure adequate sensitivity to applied forces and moments.

Embedded sensors in structures such as implants have generally decreased the mechanical properties of the composite material due to the dimensions of the sensor and wireless electronics. Machining pockets in the pre-preg tape after the pre-preg tape is wound around a mandrel also have led to an increase in the number of discontinuous fiber ends resulting in local stress risers and increased risk of an adverse biological reaction. The use of fiber optic sensors in composite structures to monitor the cure of composite materials in real time during manufacture, and to monitor the in-service structural health of composite structures have also required expensive signal processing and interrogation technology and, because of their large size, have prohibited them from being embedded into composite structures without having deleterious effects on their physical properties. In addition, fiber optic sensors have tended to induce local stress in the laminates when subjected to mechanical loads and environmental changes such as temperature and moisture making the interfaces susceptible to de-bonding, and they have exhibited poor handling characteristics, i.e., they are unlikely to survive the high temperatures and pressures associated with composite processing.

Moreover, because a strain measuring element is required to be in permanent mechanical coupling with the host structure in order to effectively transfer strain with no losses due to sliding or adhesive failure, attempts using thin film gauging methods have led to thermal damage to the polymer composite structure due to the high temperature required during the sputtering process.

Bonding to the host substrate can be achieved by integrating the strain gauge unit within the pre-preg tape in a similar manner to the reinforcing glass or carbon fibers. Integration of a fiber optic sensor directly into the main composite component, i.e. into the composite tape is another option but these devices require expensive signal processing and interrogation technology. Additionally, they are delicate structures making them less suitable for orthopaedic application.

SUMMARY

Sensors can be embedded within reinforced composite structures to enable the monitoring of biomechanical forces exerted on the structures as well as monitoring the effectiveness of the structures in use. As described further below, low-cost embedded sensor(s) can be used in, for example, filament-wound composite orthopaedic structures for measuring static and cyclic strains. The sensor(s) can be embedded within a carbon fiber reinforced polyetheretherketone (PEEK) composite component enabling the sensor(s) to function as a "smart structure." That is, the sensor(s) allows for the monitoring of the biomechanical forces exerted on the sensor(s) during, for example, fracture healing so that the sensor(s) can be used for real-time health monitoring of the structure. For example, the sensor(s) may indicate the presence of a crack or flaw that has progressed to a predetermined location on the implant.

The sensor(s) can be in the form of a wireless sensor embedded in a filament-wound composite structure designed for measuring both static and cyclic strains to enable the integrity and effectiveness of the structure to be monitored wirelessly. In some implementations, the sensor(s) or sensing element(s) is pre-packaged in a thin composite tape that can be either embedded or surface mounted on the composite structure. Having the sensor embedded in the tape resin assists in permitting strain gauges or other measuring devices to deform at the same rate and amount as control measurements, thereby providing accurate measurement of, for example, strain on the device. In other implementations, at least one sensing element in the form of a wire, plate or powder is embedded or surface mounted onto a medical composite structure to enable it to function as a smart implant. In other implementations, at least one sensor strip is electrically connected to a flexible circuit with surface mount integrated circuits utilizing "flip chip" technology, and a wireless telemetry coil embedded in a pre-preg tape to ensure that information can be wirelessly communicated with the end user. In these implementations, the sensor or sensing element may be adapted to monitor the biomechanical forces exerted on it during fracture healing if the data can be used to decouple the load sharing environment between the implant and the surrounding bone. Additionally, the sensor or sensing element may provide the end user with the integrity of the filament-wound composite structure, in terms of resisting structural cracking, delamination, or de-bonding of the fibers, avoiding catastrophic failures due to overloading of the implant. Moreover, bonding the sensor wire to the polymer matrix by heat and pressure can limit or eliminate the need for an additional bonding agent.

In one general aspect, an orthopaedic fixation device includes an inner core, a shaft being formed of a multi-layered, fiber-reinforced composite, and a sensing element embedded within the multi-layered, fiber-reinforced composite.

Implementations can include one or more of the following features. For example, the sensing element is blended into a layup structure of the multi-layered composite. The sensing element is added between layers of the multi-layered composite. The sensing element includes one of a copper wire or a biocompatible-grade barium titanate ceramic particles or PZT ceramic. The sensing element includes a wire arranged such that loads on the orthopaedic fixation device result in a change in the electrical resistance of the wire. The sensing element includes a polyimide flexible circuit embedded into the multi-layered composite or disposed in a portal defined in the composite. The flexible circuit can also be made from other materials, such as transparent conductive polyester film, screen printed silver circuits on polyester, or other applicable materials. The sensing element includes two separate circuits formed within the composite. The fixation device includes a set of longitudinally extending wires extending along a length of the shaft of the fixation device with each wire terminating at a portal defined through the composite, the each wire in the set of wires each including an electrical connection accessible through the portal such that one or more measuring devices may be connected thereto. The shaft defines a longitudinal axis, and the sensing element is oriented to detect loads occurring along the longitudinal axis. The sensing element includes a circuit that has a resonant frequency that varies in response to loading of the orthopaedic fixation device. The circuit includes a pair of conductive coils. The conductive coils are operable to wirelessly transmit radiofrequency signals. The conductive coils are operable to generate radiofrequency signals indicative of loading on the orthopaedic fixation device without a power supply embedded in the orthopaedic fixation device. One or more conductive layers are located between composite layers of the shaft. The shaft includes two or more concentric, conductive layers that extend along a length of the shaft. The sensing element is a strain gauge. The orthopaedic fixation device includes one or more conductive coils coupled to a battery, the one or more conductive coils being configured to wirelessly receive energy from an energy source and to charge the battery using the received energy. The orthopaedic fixation device includes one or more conductive coils coupled to the sensing element, the one or more conductive coils being configured to wirelessly receive energy from an energy source and to power the sensing element using the received energy.

The details of one or more implementations are set forth in the accompanying drawings and the description below. Other features, objects, and advantages of the implementations will be apparent from the description and drawings, and from the claims.

BRIEF DESCRIPTION OF THE DRAWINGS

FIG. 1 is a perspective view of a multi-layered, fiber-reinforced composite orthopaedic fixation device.

FIG. 2 is a cross-section view of the fixation device of FIG. 1.

DETAILED DESCRIPTION

To enable the monitoring of biomechanical forces exerted on structures, such as the fixation device 10 of FIG. 1, as well as monitoring the effectiveness of the structures in use, various sensing elements may be formed with or embedded between the multiple layers 12 of the fixation device 10.

Multi-layered, fiber-reinforced composite orthopaedic fixation devices are described in co-pending U.S. application Ser. No. 13/124,555, filed Apr. 15, 2011, which is hereby incorporated by reference herein in its entirety. Referring to FIGS. 1 and 2, such fixation devices 10 are formed, for example, of multiple layers 12 of a biocompatible composite material, such as PEEK and a reinforcing fiber, such as carbon fiber composite. The composite material can be a continuous fiber-reinforced material, such as a sheet, tape or tow, in which the carbon fibers are generally aligned in parallel with the length dimension of the sheet, tape, or tow.

As described further below, the multiple layers 12 may be wrapped around a sacrificial mandrel. After the implant 10 is formed, the sacrificial mandrel is removed, resulting in an implant 10 with a cannulated geometry. Alternatively, however, the implant 10 can include a solid center, a cannulated inner core, or other inner portion that remains permanently in the implant.

Figure 3:
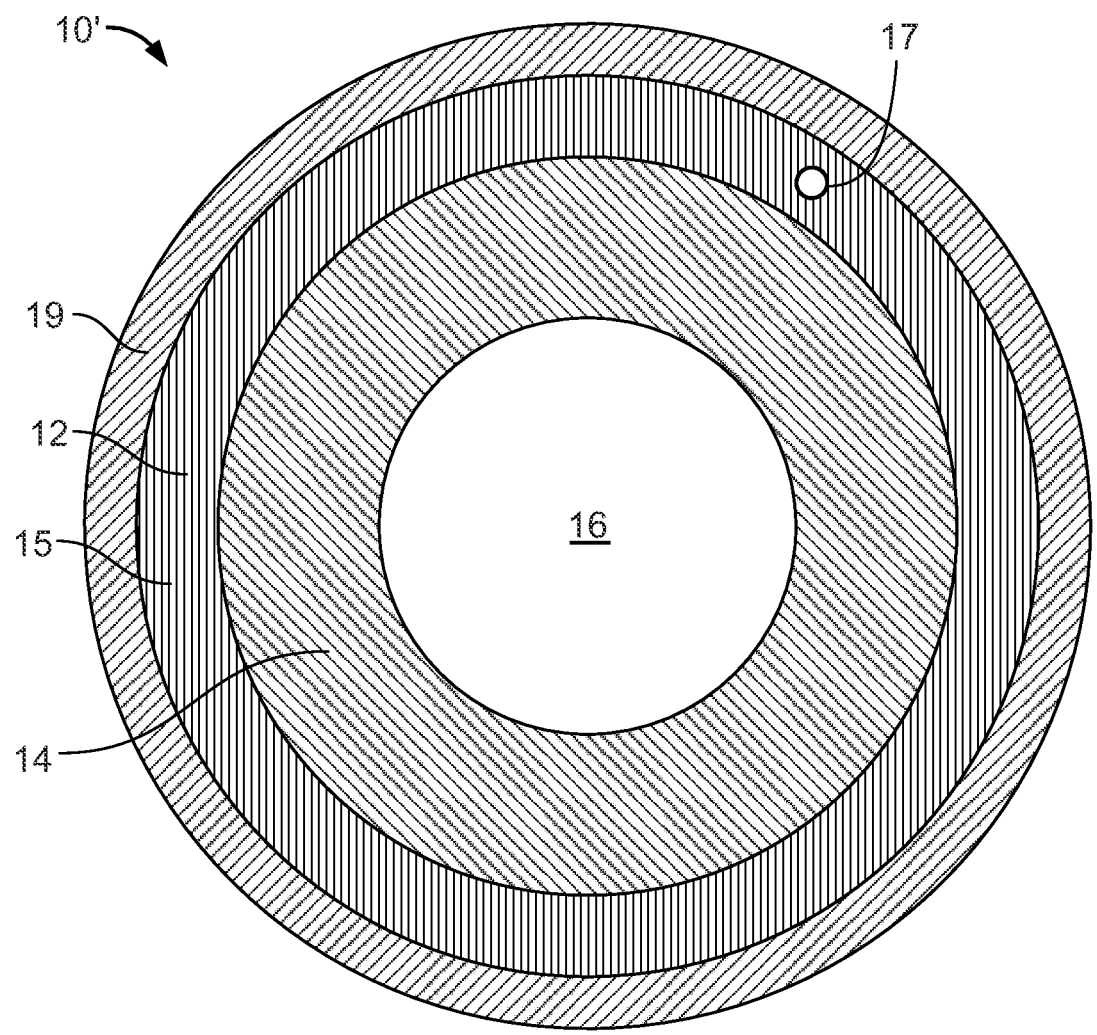
FIG. 3 is a cross-section view of an alternative fixation device.

Referring to FIG. 3, an orthopaedic fixation device 10' has an inner body 14 or inner core and an outer body 15 in the form of, for example, a shaft. In some implementations, the inner body 14 is at least partially geometrically defined by a cannulation 16.

The inner body 14 and the outer body 15 may be made from biocompatible metal or non-metal materials, such as polymers. As examples, suitable metals may be titanium, titanium alloys, steel, cobalt-chromium alloys, tantalum, magnesium, shape memory alloys, such as Nitonol. As examples, suitable polymers may be PEEK or polyarylether ketone (PAEK) also referred to as polyketones, poly-alpha-hydroxy acids, polycapropactones, polydioxanones, polyesters, polyglycolic acid, polyglycols, polylactides, polylactic acid, poly-D,L-lactic acid, poly-L,L-lactic acid, polyorthoesters, polyphosphates, polyphoesters, polyphosphonates, polysaccharides, polycaprolactone, polypropylene fumarate, polytyrosine carbonates, polyurethanes, starch, trimethylenecarbonate, monobutyrin; co-polymers; shape memory polymers.

In the depicted example, the inner body 14 is a hollow core made of metal and the outer body 15 is made of carbon-fiber, reinforced PEEK having multiple layers 12. One or more sensors are attached to or wrapped around the inner body 14, as described further below, and then covered with a protective material 19 (e.g., an injection-molded material) on the exterior of the fixation device 10'. As described further below, the multiple layers 12 can include one or more layers of a sensor tape and/or one or more sensing elements disposed between the layers 12. Also as described further below, one or more wire coils 17 can be used as sensors, embedded between the layers 12. In some implementations, the material 19 that covers the outer body 15 is an over-molded injection-mold-grade polymer (such as LT1 or LT3 PEEK-Optima products, supplied by Invibio Inc.) or a short fiber composite (such as LT1CA30, also supplied by Invibio Inc.).

In some implementations, the inner body 14 is formed of a biocompatible polymer and the outer portion 15 can be metal. As an alternative, the inner body 14 and outer body 15 can both be formed of composite materials such as carbon-fiber, reinforced PEEK. The outer body 15 is depicted as circular but may have other shapes, such as trapezoidal, square, triangular, octagonal, C-shaped, and U-shaped.

In some implementations, the composite matrix in the inner body 14 and/or the outer body 15 may be PAEK, PEEK, or another polyketone based polymers such as OXPEKK made by Oxford Performance Materials. The fiber reinforcement in the composite core could be carbon fiber, glass, Kevlar, high strength steel, fiber-drawn polyester e.g. poly(glycolic acid), or poly(lactic) acid.

The elastic modulus and/or the moment of inertia of the fixation device 10' can be adjusted by the selection of the material of the inner body 14, the diameter of the inner body 14, and the shape of the inner body 14 to hone in on the desired stiffness of the fixation device 10'.

The inner body 14 can include a fill material, for example, calcium phosphate or calcium sulfate, that is resorbed into the body after implantation providing pathways for blood flow through the fixation device 10'. The resorption of the fill material also acts to decrease the stiffness of the fixation device 10' after implantation. This is significant, as the bone should adapt to the decreasing stiffness and thus prevent or significantly reduce stress shielding.

Figure 4A:
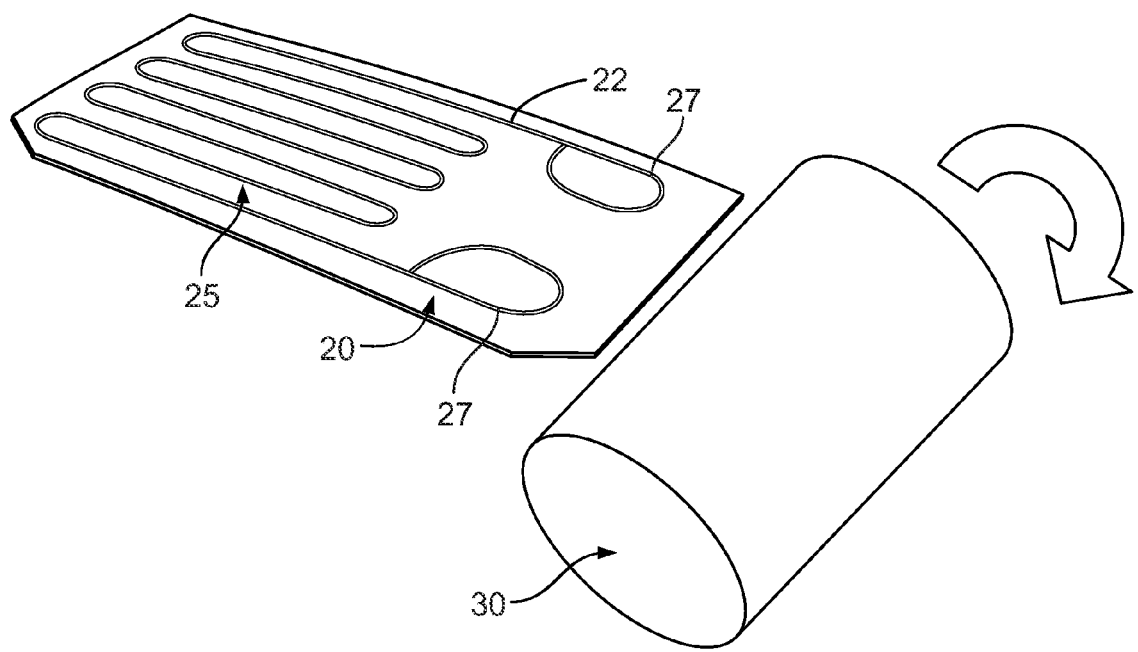
FIG. 4A illustrates a sensor in the form of a sensor tape.
Figure 4B:
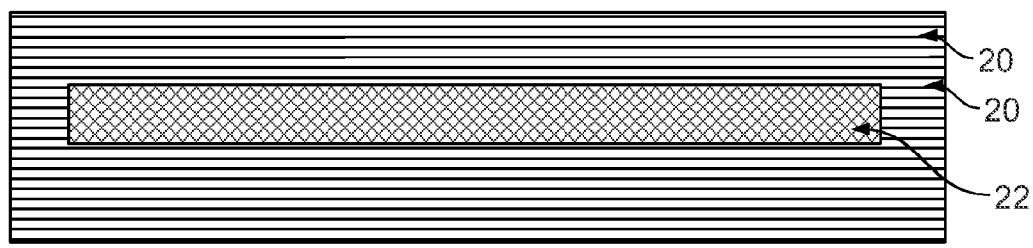
FIG. 4B is a cross-sectional end view of the sensor tape of FIG. 4A.

Referring to FIGS. 4A and 4B, a sensor tape or strip 20 may be formed onto a sacrificial mandrel 30 during manufacture of the fixation device 10. The sensor tape 20 is formed from a laminated backing partially cured with a matrix resin and then formed onto the sacrificial mandrel 30 to define the overall shape of the sensor tape 20. The sensor tape 20 includes one or more wires 22 formed in a grid-like pattern 25 on the laminated backing material of the tape 20. The wires 22 have a small transverse dimension and are selected from materials that are compatible with the resin materials (e.g., epoxy, nylon, PEEK).

For example, typical strain gauge wire materials may include combinations of tantalum, silver, gold, Constantan (copper-nickel alloy), Nichrome V (nickel-chrome alloy), and platinum alloys (usually tungsten), Isoelastic (nickel-iron alloy), or Karma-type alloy wires (nickel-chrome alloy), foils, or semiconductor materials. In the instant implementation, the wires 22 are made from copper-nickel alloys or nickel-chromium alloys. In addition, silver wires may offer certain anti-microbial properties to the PEEK device. Moreover, each strain gauge wire material has its associated characteristic gauge factor, resistance, temperature coefficient of gauge factor, thermal coefficient of resistivity, and stability.

In some instances, strain gauges are selected to withstand the processing temperature of PEEK composites. Some standard gauges (e.g., Vishay EA and CEA series) can survive up to 200° C. for short durations, for example, while curing adhesives, and are rated to 175° C. for operation. These typically include constantan foil and polyimide backing or encapsulation, and are around 56 microns thick. Other strain gauges, however, such as Vishay's WK gauges (e.g., fully encapsulated k alloy gauges with high endurance lead wires) can survive up to 400° C., making them better suited for embedding them directly into the pre-preg tape. Some high-temperature strain gauges are approximately 71 microns thick and are more brittle than standard strain gauges, reducing the volume of carbon-fiber PEEK component in the final tow.

In some implementations, Teflon (polytetrafluoroethylene) wires rated to withstand over 60° C. are used as lead wires. For example, 34AWG wires rated at 315° C. (134-AWQ) can be used. In some implementations, fiberglass wires, some of which may function reliably up to 480° C., are used.

In some implementations, high-temperature solder can be used to connect electrical components. For example, some high-temperature solders melt at between 296 and 301° C. In some implementations, silver solder can be used, which can, for example, permit reliable junctions up to between 660 and 780° C., allowing additional high-temperature processing flexibility.

Figure 5:
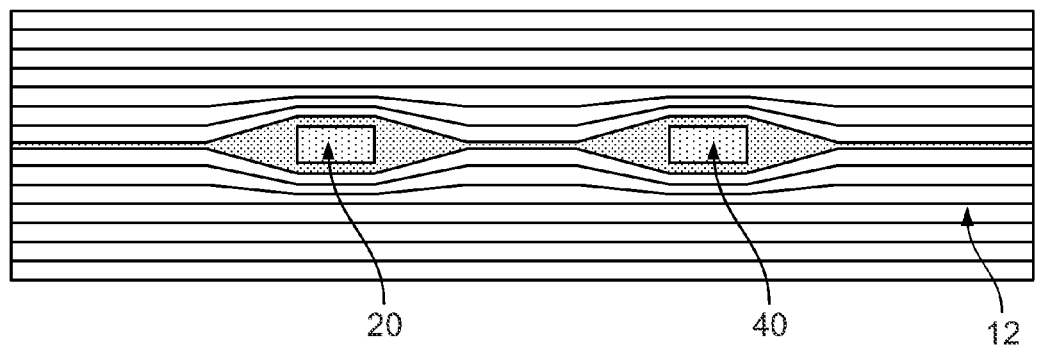
FIG. 5 is a schematic representation of a sensor embedded within the multiple layers of the fixation device.

A set of terminals 27 permit communication with one or more electrically communicative devices in order to measure and/or record, for example, the amount of strain or stress placed upon the wires 22 in use. The tape 20 with integrated strain gauge wire 22 can be used for tape winding of a structural element, or may be embedded between the different fiber layers of the structure, such as the multiple layers 12 of the fixation device 10 of FIG. 1 as depicted in FIG. 5. As shown in FIG. 5, at least two sensor strips 20, 40 may be inserted between the multiple fiber layers 12 of the fixation device 10. As a result, the sensors 20, 40 are embedded within the polymeric matrix phase of the multiple layers 12.

Figure 6:
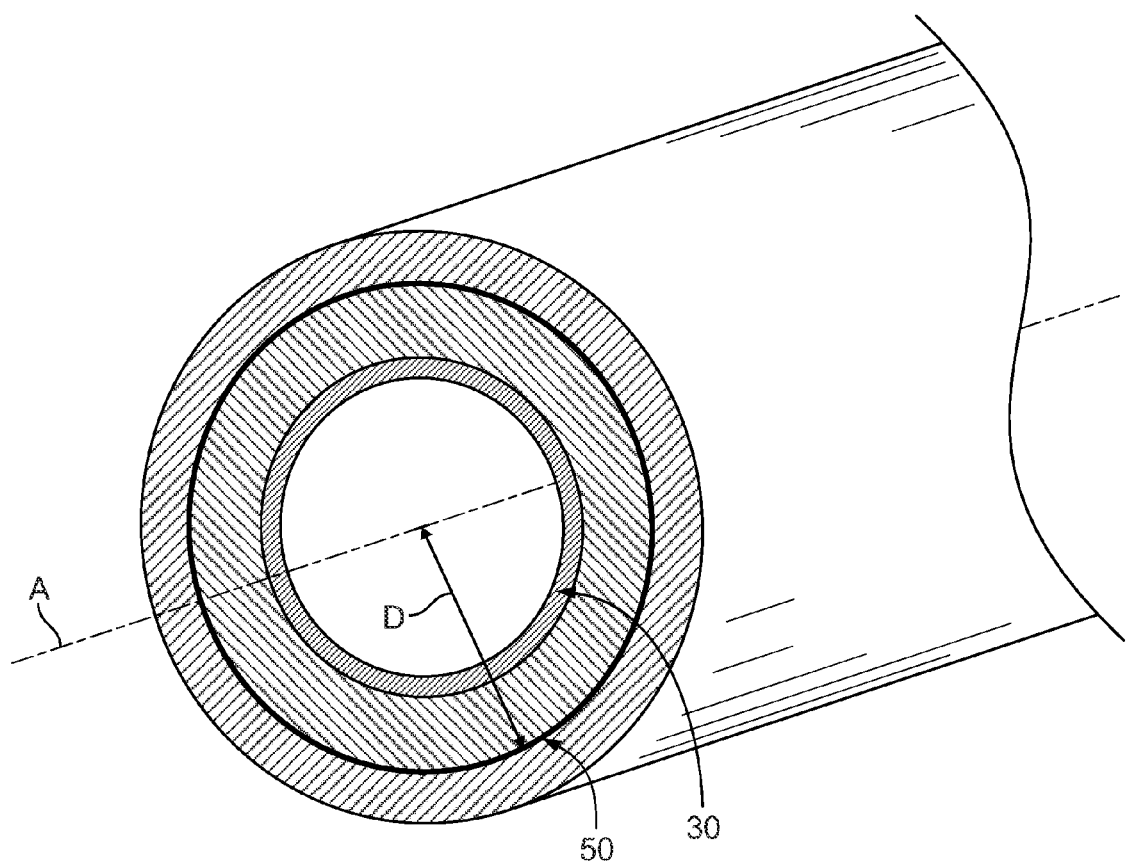
FIG. 6 is a cross-sectional end view of an alternative sensor coil arrangement.
Figure 16:
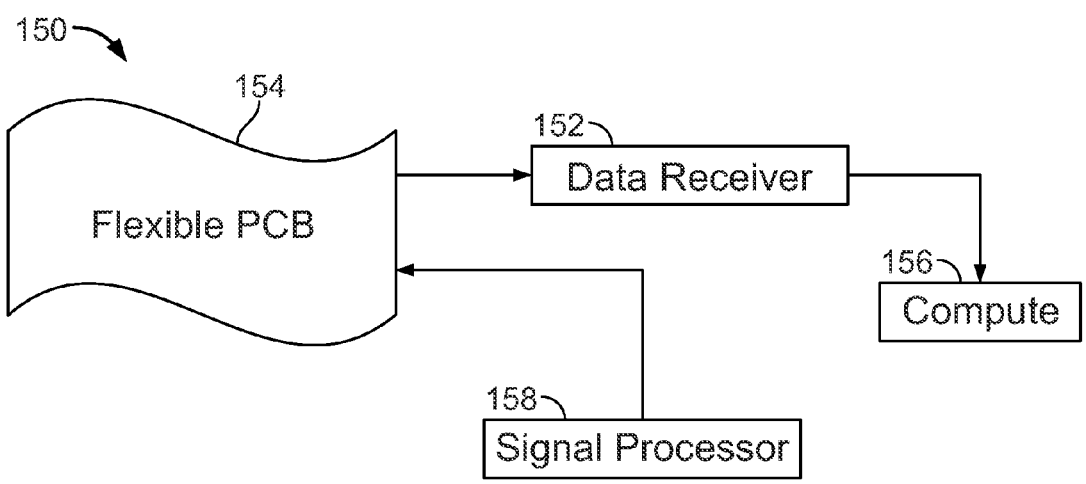
FIG. 16 is a schematic view of an electronics communication system for use with the fixation device of FIG. 1.

Referring to FIG. 6, in another implementation, a sensing element 50 includes a single copper wire arranged circumferentially around the sacrificial mandrel 30 and at a distance D from a neutral axis A. The copper wire may include a single element copper wire or may include a single woven copper wire or bundle of copper wires. The copper wire 50 is enameled and is approximately 0.025 mm thick, which is thinner than convention thermosetting tape tow (0.2 mm). Alternative materials for use in forming sensing element 50 include nickel, gold, or platinum. During use, loading of the fixation device 10 may result in a change in the tension of the copper wire 50. For example, if the wire 50 increases in length and its cross-sectional area is reduced through external loading, a change in electrical resistance in proportion to the strain sensitivity of the wire's resistance may be detected by a data receiver 152 (FIG. 16) and recorded by a recording device, such as a computer 156 (FIG. 16).

Figure 7:
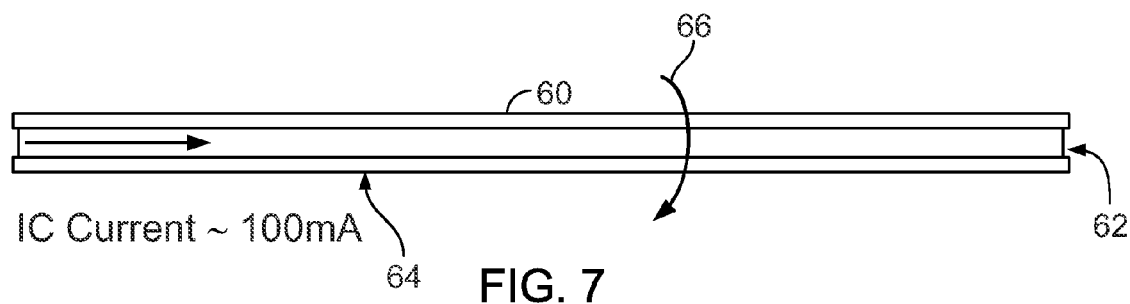
FIG. 7 is an alternative implementation of the sensor coil arrangement of FIG. 6.

Referring to FIG. 7, in another implementation, a sensing element 60 includes a copper wire 62 formed with an electrodeposited thin layer 64 (e.g., 10-20 microns) of a magnetic elastic material (e.g., nickel-iron alloy) that vibrates in response to an AC magnetic field. The thin layer 64 of the magnetic elastic material exhibits a magnetic field 66 with characteristics that change with an applied stress. For example, to operate the sensing element 60, an AC current of approximately 100 mA or more is passed through the magnetized wire 62. The current has a signature output frequency, which changes when the wire 62 is stressed. This change may be detected by a data receiver 152 (FIG. 16) and recorded by a recording device, such as a computing device 156 (FIG. 16).

Any of the sensing elements discussed above may be installed at any location along the fixation device 10 or test structures such as a hollow cylinder having an internal diameter of about 4.5 mm and an outer diameter of about 10 mm designed to test the sensing elements under certain conditions. Examples of locations may include weak points or areas of high stress, such as screw or fastener holes in the proximal or distal ends of the device or areas where the diameter or thickness of the device changes. Signals from the sensing elements can serve to monitor and/or diagnose fracture healing or to alert an operator to incipient component failure. In addition, signals from the sensing elements may be received by a handheld field generator in order to assist the surgeon in locating various landmarks on the fixation device 10 or test structure. The precise location of the sensor can be achieved with the assistance of Finite Element Analysis (FEA) simulations, CT, or MRI scans. For example, imperfect fiber alignment could heavily influence their associated sensor and/or actuation performance. For example, the embedded sensor can have preferred orientation/axes with respect to the direction of the fibers. If there are significant variations within the fiber structure, this may affect the sensitivity of the sensor in response to an applied load.

Figure 8:
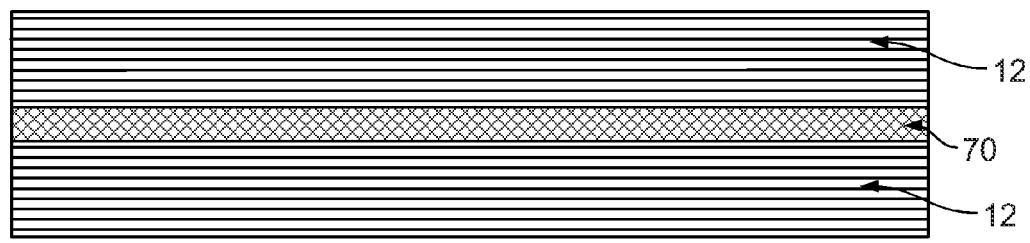
FIG. 8 is a schematic representation of an implementation for embedding sensor coils within the composite structure of FIG. 1.
Figure 9:
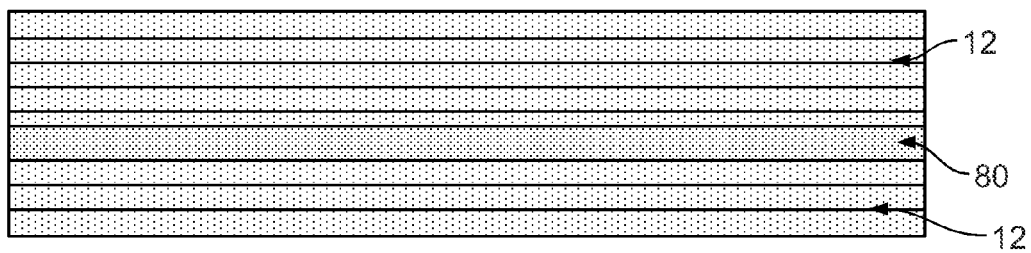
FIG. 9 is a schematic representation of an alternative implementation for embedding sensor coils within the composite structure of FIG. 1.

Referring to FIGS. 8-11, there are provided various options for embedding sensing elements within the composite structure of, for example, the fixation device 10. As shown in FIGS. 8 and 9, a copper wire 70 and biocompatible-grade barium titanate ceramic particles or PZT ceramic 80, respectively, are embedded within the multiple layers 12 of the biocompatible PEEK using a combination of heat and pressure, or alternatively, using an adhesive between the layers. PEEK is a high melting point material that has a melting point of approximately 340° C. and therefore should be processed at 360° C. to 400° C. to enable incorporation of the ceramic powder and extruding or molding of the composite blend. The ceramic powder is heated to about 400° C. at atmospheric pressure, and held at this temperature for sufficient time for the bound water to be released. If the powder is spread thinly, moisture release will be more efficient, and a holding time of about 30 to about 60 minutes is suitable. Ceramic powder is added (between 0.01 to about 20.0 wt %) to the PEEK polymer in the molten state between 343° C. and 400° C. at ambient pressure. This thermal treatment will also remove moisture, which will minimize the size and number of any voids in the material, which maintains the mechanical properties of the final product. The biocompatible-grade barium titanate ceramic particles or PZT ceramic particles exhibit high piezoelectric and electromechanical coupling coefficients, such as, electromechanical coupling constant ($k_{ss}$) of less than about 0.53 and distortion/charge constant ($d_{ss}$) of less than about 2.24 E-10 pm/V. The copper wire 70 and biocompatible-grade barium titanate ceramic particles or PZT ceramic 80 may be blended into the layup structure of the multiple layers 12. In this implementation, the sensing elements 70, 80 are embedded into the composite laminate, and so are protected by the same laminate.

Figure 10:
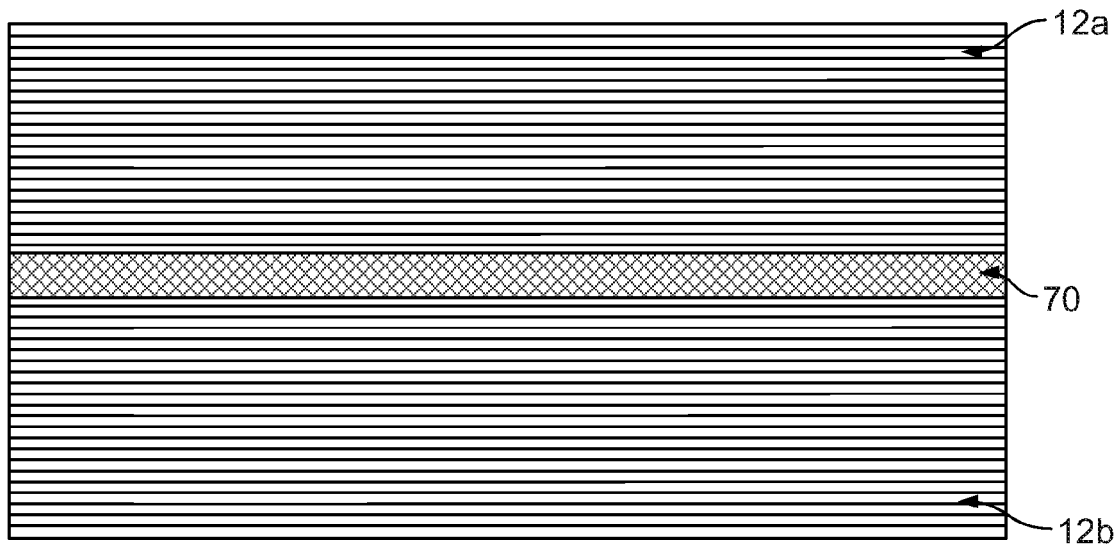
FIG. 10 is a schematic representation of a further alternative implementation for embedding sensor coils within the composite structure of FIG. 1.
Figure 11:
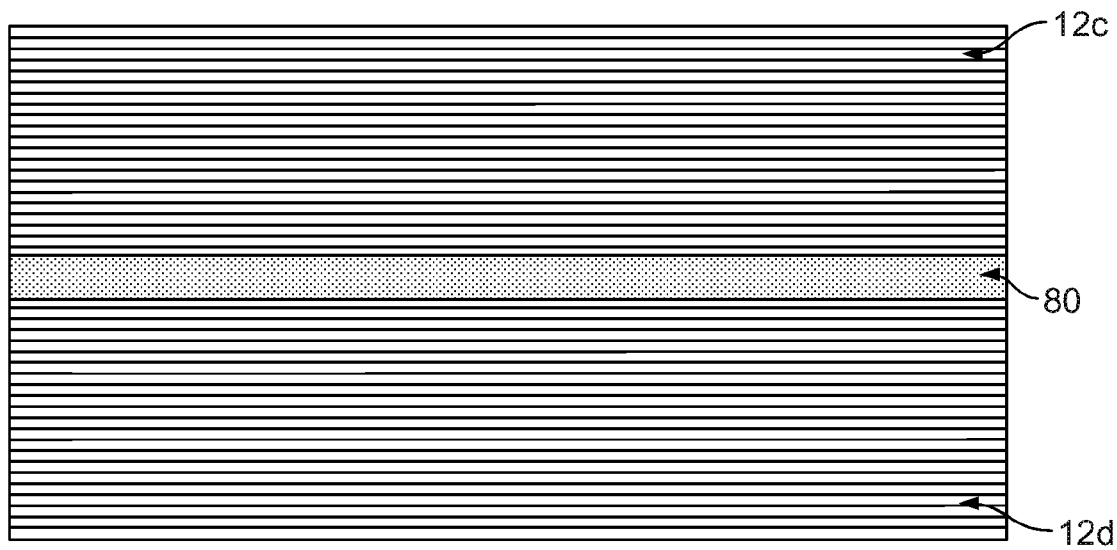
FIG. 11 is a schematic representation of a further alternative implementation for embedding sensor coils within the composite structure of FIG. 1.

Alternatively, as shown in FIGS. 10 and 11, the copper wire 70 and biocompatible-grade barium titanate ceramic particles or PZT ceramic 80 may be sandwiched between two layers of multiple layers 12a-12d, respectively, using a combination of heat and pressure. In such an implementation a first set of multiple layers, such as multiple layers 12a can be formed then the copper wire 70 is added, and then the second set of multiple layers 12b can be formed over the copper wire 70 to sandwich the copper wire between the sets of multiple layers 12a, 12b. This method of embedding the sensor is compatible with existing commercial grade CFR PEEK tape, and helps to ensure that the optimized lay-up structure and mechanical performance of the final device are maintained.

Figure 12:
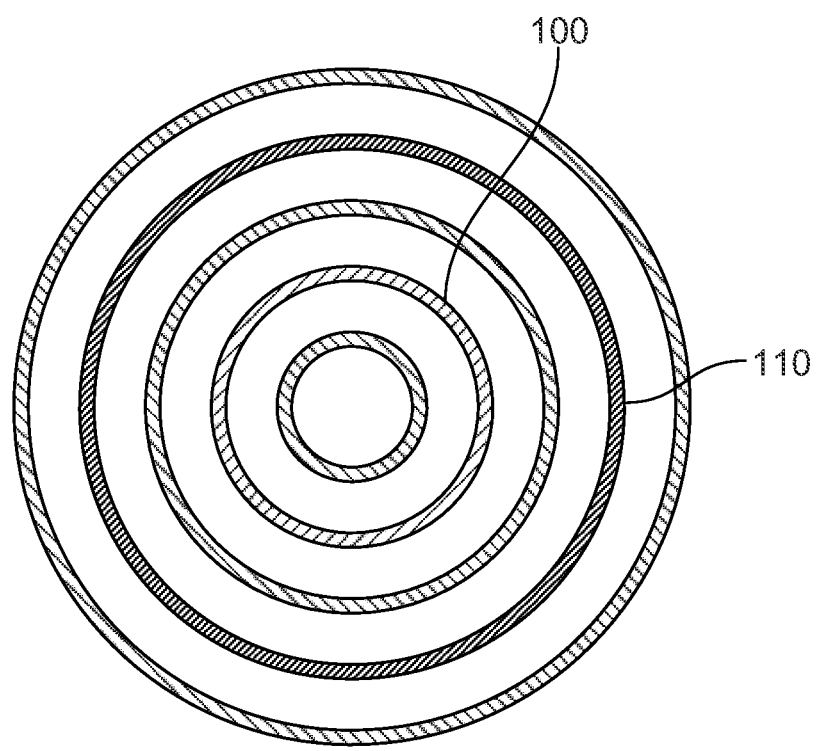
FIG. 12 is a schematic end view of a fixation device.

Referring to FIG. 12, the fixation device 10 may be formed with multiple sensing elements forming one or more sensing circuits 100, 110 integrated into the body of the device 10. Again, the fixation device 10, such as an intramedullary nail, can be created when a pre-preg tape is wound preferably around a mandrel. During this process, one or more conductive tapes can also be wound to create one or more layers or circuits 100, 110 of a conductive material along the length of the device 10 and between or within the multiple composite layers 12 of the fixation device 10. This provides a convenient way of adding electronic components to the device 10. For example, instead of requiring wires that run the length of the device, various layers or circuits 100, 110 may be used to support the electronic components. For example, at one end of the device 10, a power source (not shown) may be integrated with, coupled to, or in contact with the device 10. The power source is attached so that supply voltage is coupled to at least one of the layers or circuits 100, 110 and a ground is coupled to the other of the layers or circuits 100, 110. Therefore, a component may be added at any location on the device 10. During the manufacturing process, if a component needs to be added to the device 10, a pocket or hole may also be created to place the components. Wherever the component is positioned, separate cavities can be created at depths to intersect with the conductive layers 100, 110. One lead of the component can be connected to one of the conductive layers 100, 110, and the other lead connected to the other of the conductive layers 100, 110. Such a configuration provides a simpler manufacturing process when compared to using wires to power a component or to transmit electrical energy. For example, it is often difficult to locate the wires in the device used to connect the various components.

The multiple sensing circuits or layers 100, 110 may be connected to one or more devices, such as an accelerometer, a strain gauge, or the like to transmit measurements to a receiving device (not shown) to permit a user to measure and make determinations as to the performance of the sensing elements or the fixation device 10. As discussed above, the sensing elements and associated circuits 100, 110 may be formed at any points along the fixation device 10 that are deemed critical to functionality or areas in which the user wants to monitor performance characteristics of the structure.

Figure 13:
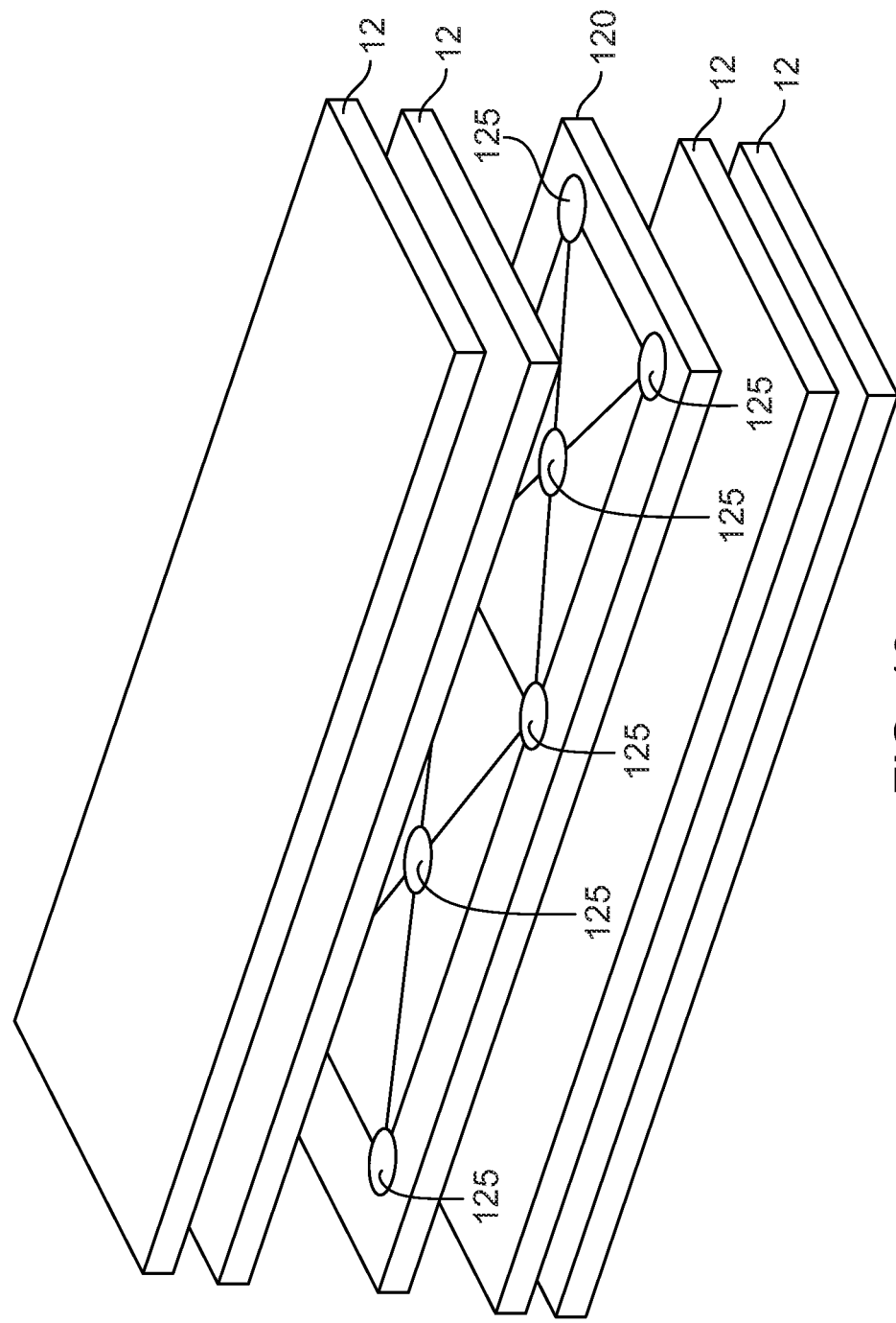
FIG. 13 is a perspective view of a flexible circuit for use with the fixation device of FIG. 1.

Referring to FIG. 13, there is shown an alternative sensing element in the form of a flexible circuit, and specifically, a polyimide flexible circuit 120. The flexible circuit 120 may be embedded into the composite layers 12 during, for example, the tape winding operation of the fixation device 10 as shown in FIG. 13. In this implementation, the flexible circuit 120 is co-cured with the composite layers 12. The flexible circuit 120 may include one or more elements 125, such as strain gauges or accelerometers, in order to provide signals to a receiving device to enable a user or equipment to monitor the performance of the fixation device 10 or structure to which the sensing elements are mounted.

Figure 14:
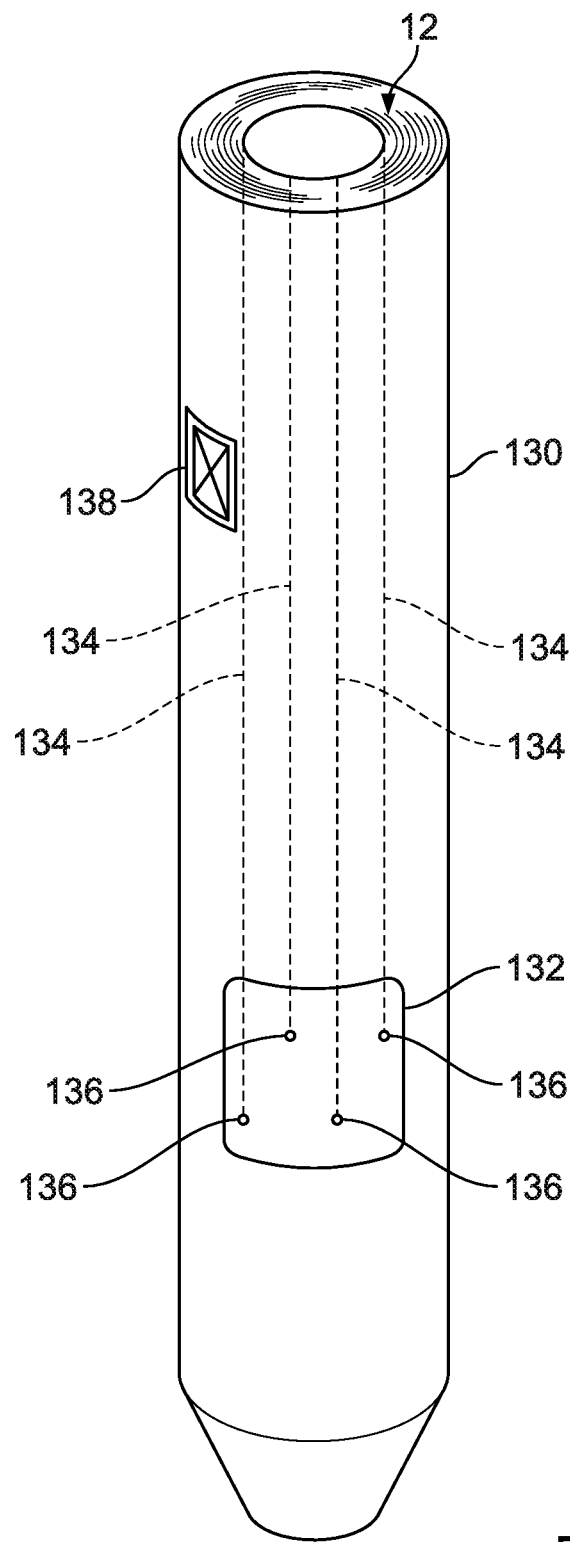
FIG. 14 is a front perspective view of a fixation device.

Referring to FIG. 14, alternatively, the flexible circuit 120 may be located in a portal, such as portal 132 formed in a wall of the device, such as fixation member 130. The portal 132 is created after removal of a sacrificial mandrel following the tape winding operation of the fixation device 130. As shown in FIG. 14, the flexible circuit may be connected to multiple wires 134 extending longitudinally through the multiple layers 12 of the fixation device 130. These wires, in turn, may be connected to one or more receiving devices for measuring, recording, or analyzing the data received from the flexible circuit 120. In addition to, or in lieu of locating the flexible circuit 120 within the portal 132, the portal may be provided with a set of electrical contacts or pads 136 for optionally connecting additional measuring devices, such as strain gauges, accelerometers and the like to one or more receiving devices.

FIG. 14 also illustrates an RFID chip 138 embedded in the fixation device. As an example, the RFID chip 138 may be inserted in between layers 12 as the fixation device is formed. In another implementation, a pocket is formed by machining or thermoforming, and the RFID chip 138 is placed in the pocket. The RFID chip 138 may also be attached to one or more of the sensing circuits or the flexible circuits described herein.

Figure 15:
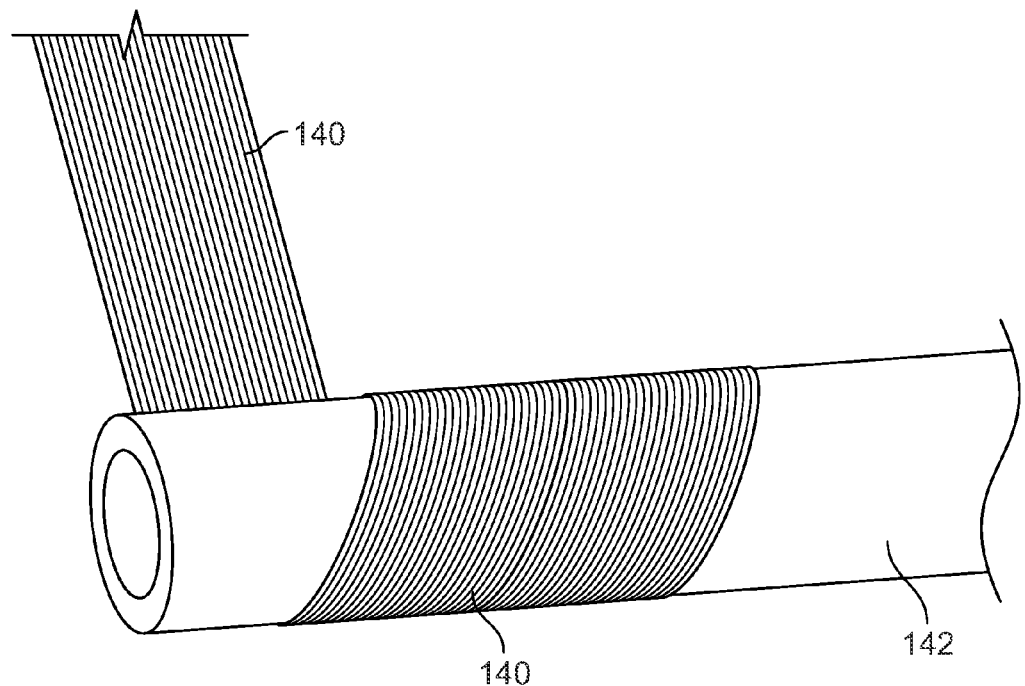
FIG. 15 is a perspective view of a telemetry coil for use with the fixation device of FIG. 1.

In addition to the various sensing elements described herein, the fixation device 10 or test structures may also include one or more coils adapted for wireless energizing and/or data reading from the one or more sensing elements located on the fixation device 10 or test structure. Referring to FIG. 15, there is shown an exemplary telemetry coil 140 in the process of being wound around a sacrificial mandrel 142. The telemetry coil 140 includes an enameled copper coil that is wound onto the outer surface of the polymer composite implant, such as fixation device 10, at the end of the implant. Locating the coil at the end of the implant generally avoids unwanted electromagnetic interference issues with the underlying carbon fiber layers 12. For example, placing the telemetry coil 140 as close to the outer surface of the device as possible, helps limit any losses incurred from the conductive effect of the carbon fibers. Additionally, the copper wire can be impregnated in polymer matrix and then wound onto the mandrel making it easier to wind, help insulate the wire from the underlying carbon fiber layers, and protect it from moisture ingress. The coil winding procedure can be added during the overmolding step, which is used to protect the carbon fibers and add pigmentation for product differentiation.

Referring to FIG. 16, there is shown a schematic of an exemplary hardware system 150 which can be employed with any one of the sensing elements and assemblies described herein. The hardware system 150 includes a data receiver 152 coupled between a flexible printed circuit board 154, which may include one or more of strain gauges, accelerometers, or other measuring devices, and a computing device 156. A signal processor 158 is coupled to and sends signals to the flexible printed circuit board 154, which then may use such signals to generate one or more data signals that are received by the data receiver 152 and communicated to the computing device 156. The computing device 156 may include one or more processors or sub-units for analyzing the data received from the flexible printed circuit board 154 and communicating that data to a user via, for example, a graphical user interface coupled to the computing device or to a printer or storage device coupled to the computing device.

Figure 17:
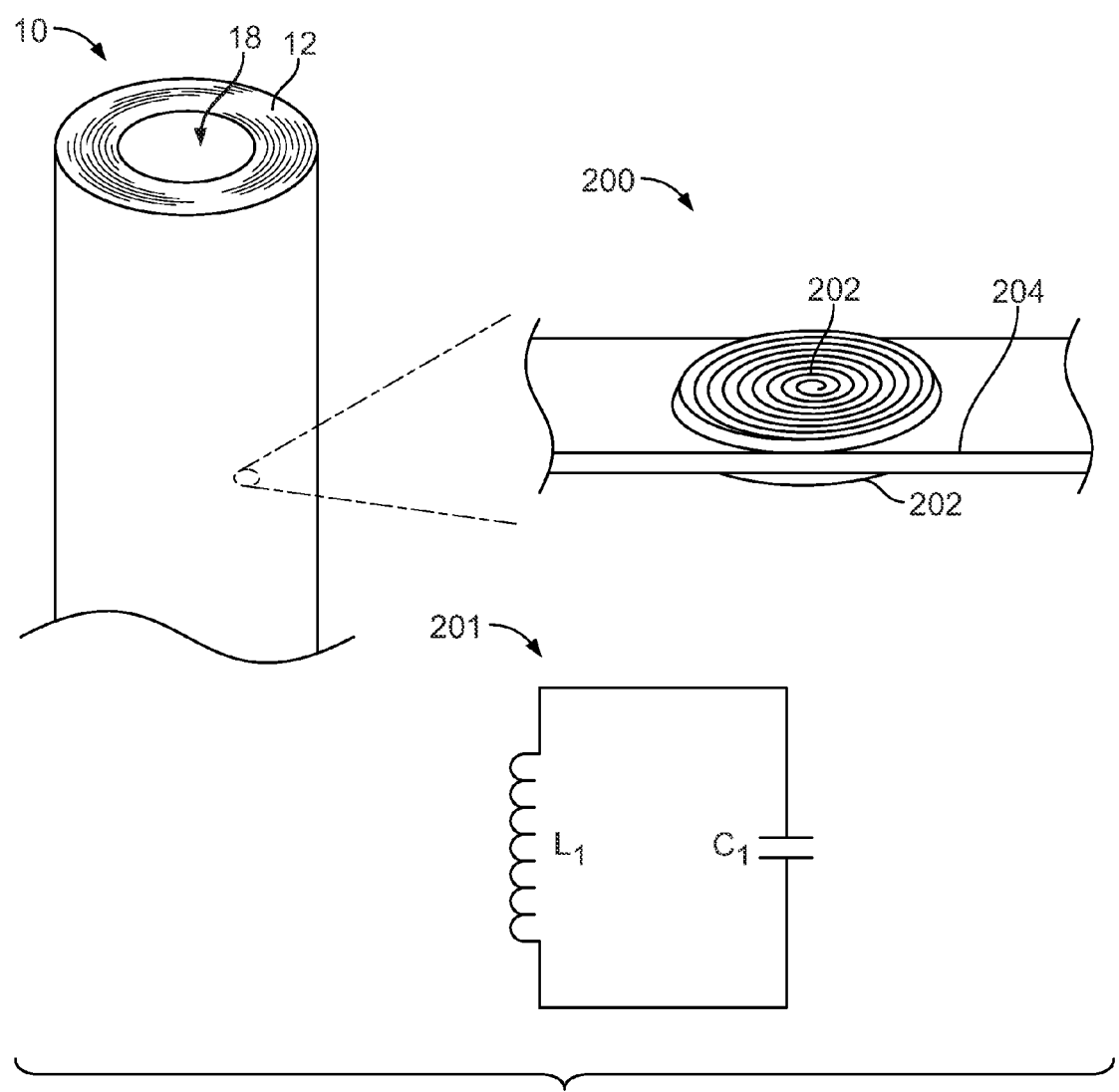
FIG. 17 is a schematic representation of alternative implementation for embedding sensor coils within the composite structure of FIG. 1.

Referring to FIG. 17, in some implementations, a resonant or tuned circuit 200 is used as a sensing element. The resonant circuit can be used instead of a sensor that requires associated electronics, such as a circuit board, surface-mount components, and a telemetry coil. The resonant circuit 200 can include a pair of conductive coils 202, for example, a pair of flat-wound copper wire coils separated by a dielectric material 204. Together, the coils 202 act as an inductor, $L_1$, and a capacitor, $C_1$, in the resonant circuit 200 (e.g., an inductive/capacitive or L-C resonant circuit). A circuit diagram 201 of the resonant circuit 200 is illustrated in FIG. 17. In some implementations, the coils 202 are formed of copper wire having a diameter between 30 and 40 AWG. For example, copper wire with a diameter of 36 AWG (0.127 mm) can be used. Copper wire coated in enamel can be used in the coils 202. The outer diameter of the coils 202 can be between, for example, approximately 4 mm and approximately 10 mm.

In some implementations, the resonant circuit 200 does not require additional implantable electronics to provide power or to perform processing of sensor signals. As a result, the resonant circuit 200 may occupy a volume smaller than other sensor circuits that include other associated electronic components. A single resonant circuit 200 using a pair of conductive coils 202 can provide a single-channel wireless telemetry system. The single-channel system is typically adequate for monitoring of a composite device if loading of the composite device is occurs principally in one direction (e.g., along a single axis).

The resonant circuit 200 can be excited by an external radiofrequency field. The radiofrequency field provides the power to the resonant circuit 200, so the resonant circuit 200 is can operate without a power supply embedded in the fixation device 10. In response to the external field, the resonant circuit 200 resonates at a characteristic resonant frequency and emits a radiofrequency signal at the resonant frequency. The resonant frequency can be detected with an external antenna placed around the patient's limb, and an oscilloscope or other measuring device can be used to monitor changes in the resonant frequency.

The resonant frequency, F, of the resonant circuit 200 can be expressed in terms of inductance, L, and capacitance, C, of the resonant circuit 200 by the relation:

$$F = \frac{1}{2\pi\sqrt{LC}}$$

In the resonant circuit 200, the inductance, L, is substantially constant. However, changes in the spacing between the coils 202 change the capacitance, C, which, in turn, changes the resonant frequency, F. External loading of the composite fixation device 10 including the resonant circuit 200 (for example, axial compression of the fixation device 10) changes the spacing between the coils 202 in the resonant circuit 200. The sensitivity of the resonant circuit 200 to an applied load can be modified by changing the dielectric properties of the material placed between the coils 202.

In some implementations, multiple resonant circuits 200 are located within the structure of the composite fixation device 10. The different resonant circuits 200 can be arranged in different orientations to provide sensitivity to different types of applied loads. For example, resonant circuits 200 can be included to detect forces exerted on the fixation device 10 along, for example, up to six degrees of freedom. The fixation device 10 can include one or more resonant circuits 200 to facilitate measurement of forces along one or more of the six degrees of freedom. In some implementations, each resonant circuit 200 detects forces in a different direction. Three orthogonal axes, X, Y, Z, can be defined relative to the fixation device 10, with the Z-axis extending along a longitudinal axis of the fixation device 10. Force along each axis X, Y, Z, (e.g., forces $F_x$, $F_y$, $F_z$, respectively) can be detected by a different resonant circuit 200. Rotational force about each axis, X, Y, Z, (e.g., forces $M_x$, $M_y$, $M_z$, respectively) can also be detected by a different resonant circuit 200. Thus six resonant circuits 200 can be used to detect forces in six degrees of freedom (e.g., $F_x$, $F_y$, $F_z$, $M_x$, $M_y$, $M_z$). As a result, the fixation device 10 can facilitate monitoring of bending moment ($M_x$, $M_y$), axial force ($F_z$), shear forces ($F_x$, $F_y$), and/or torsional force ($M_z$).

Separate external antenna coils can be used to differentiate the signals received from each resonant circuit 200. In some implementations, each telemetry channel is multiplexed and processed separately so that the frequency shifts that correspond to each resonant circuit 200 are determined.

In general, sensors and other electronics in the orthopaedic implant 10, 10' may be powered through inductive coupling with an external power source. In some implementations, one or more power transfer coils are included in the orthopaedic implant 10, 10', for example, embedded between layers 12 of composite material. The power transfer coils wirelessly receive energy from a nearby electromagnetic field generator. In some implementations, the coils 202 of the resonant circuit 200 act as power transfer coils to receive power for other electronic components. The orthopaedic implant 10, 10' uses the received energy to power a sensor, a telemetry component, a recording device, a processor, and/or other electronics. The received energy may also be used to charge a battery, which may be located in the orthopaedic implant 10, 10'.

Other implementations are within the scope of the disclosure. For example, the telemetry coil 140 (FIG. 15) may be located at a location other than the end of the implant so long as the location of the coil avoids or limits electromagnetic interference issues. The signal processor 158 (FIG. 16) may be coupled to the computing device 156 such that the computing device 156 may send appropriate control signals to the signal processor 158 or receive signals or data from the signal processor 158. In addition, although the mandrel has been described as a "sacrificial" mandrel, in some implementations the mandrel may be a permanent part of the orthopaedic device or may be removable from the device either before or after insertion of the device. Moreover, although the implementations described herein have been in the context of intramedullary nail implants, the disclosed implementations may also be used in other orthopaedic devices, such as bone plates, hip implants, and other devices, used for example, in knee, shoulder, or hip replacement techniques or surgical procedures. Accordingly, other implementations are within the scope of the disclosure and the following claims.

What is claimed is:

1. An orthopaedic fixation device, comprising:
an inner core;
a shaft being formed of a multi-layered, fiber-reinforced composite; and a sensing element embedded within the multi-layered, fiber-reinforced composite.

2. The orthopaedic fixation device of claim 1, wherein the sensing element is blended into a layup structure of the multi-layered composite.

3. The orthopaedic fixation device of claim 1, wherein the sensing element is added between layers of the multi-layered composite.

4. The orthopaedic fixation device of claim 2, wherein the sensing element comprises one of a copper wire or a biocompatible-grade barium titanate ceramic or PZT ceramic.

5. The orthopaedic fixation device of claim 1, wherein the sensing element comprises a wire arranged such that loads on the orthopaedic fixation device result in a change in the electrical resistance of the wire.

6. The orthopaedic fixation device of claim 1, wherein the sensing element comprises a polyimide flexible circuit embedded in the multi-layered composite or disposed in a portal defined in the multi-layered composite.

7. The orthopaedic fixation device of claim 1, wherein the sensing element comprises two separate circuits formed within the multi-layered composite.

8. The orthopaedic fixation device of claim 1, further comprising a set of wires extending longitudinally along a length of the shaft of the orthopaedic fixation device such that each wire terminates at a portal defined through a portion of the multi-layered composite, each wire in the set of wires comprising an electrical contact accessible through the portal such that one or more measuring devices can be connected thereto.

9. The orthopaedic fixation device of claim 1, wherein the shaft defines a longitudinal axis, and the sensing element is oriented to detect loads occurring along the longitudinal axis.

10. The orthopaedic fixation device of claim 1, wherein the sensing element comprises a circuit that has a resonant frequency that varies in response to loading of the orthopaedic fixation device.

11. The orthopaedic fixation device of claim 10, wherein the circuit comprises a pair of conductive coils.

12. The orthopaedic fixation device of claim 11, wherein the conductive coils are operable to wirelessly transmit radiofrequency signals.

13. The orthopaedic fixation device of claim 11, wherein the conductive coils are operable to generate radiofrequency signals indicative of loading on the orthopaedic fixation device without a power supply embedded in the orthopaedic fixation device.

14. The orthopaedic fixation device of claim 1, wherein one or more conductive layers are located between composite layers of the shaft.

15. The orthopaedic fixation device of claim 1, wherein the shaft comprises two or more concentric, conductive layers that extend along a length of the shaft.

16. The orthopaedic fixation device of claim 1, wherein the sensing element is a strain gauge.

17. The orthopaedic fixation device of claim 1, further comprising one or more conductive coils coupled to a battery, the one or more conductive coils being configured to wirelessly receive energy from an energy source and to charge the battery using the received energy.

18. The orthopaedic fixation device of claim 1, further comprising one or more conductive coils coupled to the sensing element, the one or more conductive coils being configured to wirelessly receive energy from an energy source and to power the sensing element using the received energy.

19. The orthopaedic fixation device of claim 3, wherein the sensing element comprises one of a copper wire or a biocompatible-grade barium titanate ceramic or PZT ceramic.

* * * * *